US00PP09312P

United States Patent [19]

Dehan

[11] Patent Number: Plant 9,312

[45] Date of Patent: Oct. 3, 1995

[54] GYPSOPHILA PLANT NAMED 'MAGIC ARBEL'

[75] Inventor: Klara Dehan, Holon, Israel

[73] Assignee: Danziger "Dan" Flower Farm, Post Beit Dagan, Israel

[21] Appl. No.: 299,617

[22] Filed: Sep. 2, 1994

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 8,651 3/1994 Dehan ..... Plt./68.1

*Primary Examiner*—James R. Feyrer

*Attorney, Agent, or Firm*—Foley & Lardner

[57] ABSTRACT

A new and distinct cultivar of Gypsophila plant named Magic Arbel, characterized by its relatively large flowers, white flower color; excellent branching; floriferous habit; continuous flowering in Israel from April to late fall; and its suitability for cut flower production.

1 Drawing Sheet

The present invention relates to a new and distinctive cultivar of Gypsophila plant, referred to by the cultivar name Magic Arbel.

The new cultivar was developed by the inventor Klara Dehan in Mishmar Hashiva, Israel through controlled breeding by crossing male and female parents which are unknown at this time. Both parents were selected seedlings from the breeding of grandparents which are likewise unknown at this time. Both the parents and grandparents are proprietary lines used exclusively for breeding.

Asexual reproduction by leaf cuttings taken by the inventor at Mishmar Hashiva, Israel has shown that the unique features of this new Gypsophila are stabilized and are reproduced true to type in successive propagations.

The following characteristics in combination distinguish the new gypsophila from other cultivated gypsophila of this type known and used in the floriculture industry:

1. Round flower form.
2. White flower color.
3. Flowers are relatively large and carried on long sturdy stems.
4. Floriferous habit, with many flowers being in bloom and bud at one time.
5. In Mishmar Hashiva, Israel, the new cultivar flowers continuously in natural season from April to late fall.
6. Excellent branching, particularly if plants are pinched 3–4 weeks after planting cuttings.
7. Magic Arbel possesses day neutrality, that is, it will respond to lower levels of light for flowering. Thus, under natural outdoor light conditions, Magic Arbel will flower earlier in the spring and very late in the fall or early winter.
8. The new cultivar is particularly suited for cut flower production.

The accompanying colored photograph illustrates the branching and flowering characteristics of Magic Arbel, showing the colors as true as it reasonably possible to obtain in a colored reproduction of this type.

The new cultivar can be compared in certain traits to the unpatented cultivar Perfecta, a commercial cultivar well known in Israel. With regard to flowering, under the same temperatures and day length, Magic Arbel will reach flowering faster, particularly in the spring and fall, due to the ability of Magic Arbel to induce flowering under shorter day lengths. For example, in November with a day length of 10.5 hours in Israel, Magic Arbel will flower and Perfecta will not. Magic Arbel produces about 20% fewer flowering stems per flash than Perfecta, under the same growing conditions.

The following is a detailed description of the new cultivar based on plants produced in an open field in accordance with commercial practices in Mishmar Hashiva, Israel.

Color references are made to the Royal Horticultural Society Colour Chart (RHS) except where general terms of ordinary dictionary significance are used.

Parentage: Both male and female parents are unknown.

Propagation: By leaf cuttings; rooting is quick and uniform, initiated in 7–8 days at 30° C. in summer and 8–10 days at 20° C. in winter.

PLANT DESCRIPTION

A. Form: Relatively tall, upright; excellent for cut flower propagation.

B. Habit of Growth: Fast growing and excellent branching. When grown in Israel under average winter temperatures of approximately 10° C. and under normal field conditions, the height of the new cultivar is approximately 80 cm. Flowering is early since Magic Arbel has been shown to be less responsive to daylength than other cultivars in this class. The plant is perennial in Israel where average winter temperatures are approximately 10° C.

C. Foliage:
   1. *Size.*—Leaves are approximately 8 cm in length and 1.2 cm in width; very few leaves appear on flowering stems.
   2. *Shape.*—Lanceolate.
   3. *Margin.*—Entire.
   4. *Color.*—Top side: 147A. Underside: 147A.
   5. *Venation.*—Palmate, but very inconspicuous with a prominent midrib.

FLOWERING DESCRIPTION

A. Natural flowering season: In Israel under outdoor conditions, flowering starts in April and continues until late fall.

B. Flower buds: Closed buds are spherical and approximately 2 mm in diameter. Involucre has 8 leaves, each approximately 0.7 mm wide and 2.5 mm long.

C. Flowers borne: On relatively long, strong stems.

D. Quantity of flowers: Very floriferous; a total of approximately 1300–1500 flowers are produced on one flowering stem.

E. Petals:
   1. *Shape.*—Generally round.
   2. *Color.*—155D, fading to very pale pink in low temperatures.
   3. *Number of petals.*—Approximately 20 per flower.
   4. *Size of flowers.*—Approximately 1.1 cm in total diameter.

F. Reproductive organs: Flowers are monoecious.

1. *Stamens.*—5 anthers, relatively thin and white in color; pollen is white.
2. *Pistils.*—Stigma is cone shaped and light green in color; style is light green in color; there are five ovaries 1–2 mm and light green in color.

G. Disease resistance: Magic Arbel has not been shown to be sensitive to botrytis or other common diseases.

H. Fertility: Male and female sterile.

I claim:

1. A new and distinct cultivar of Gypsophila plant named Magic Arbel, as illustrated and described.

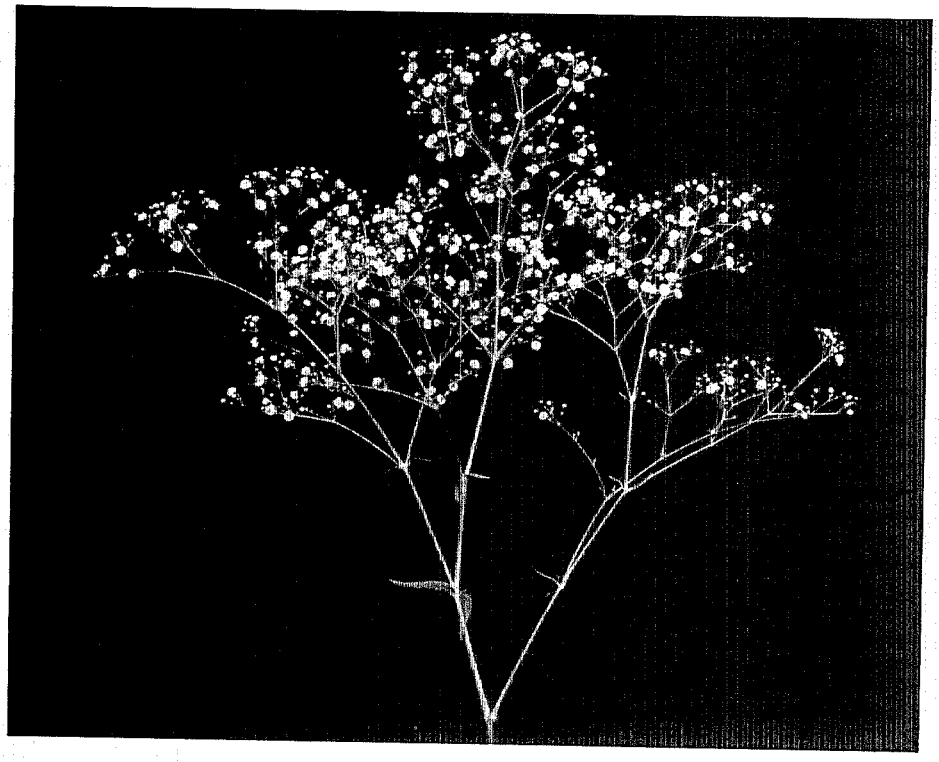

* * * * *